(12) United States Patent
Selikowitz

(10) Patent No.: US 7,727,140 B2
(45) Date of Patent: Jun. 1, 2010

(54) SURGICALLY IMPLANTABLE PERINEAL URINARY INCONTINENCE DEVICE

(75) Inventor: Stuart M. Selikowitz, Etna, NH (US)

(73) Assignee: Department of Veterans Affairs, Washington, DC (US)

( * ) Notice: Subject to any disclaimer, the term of this patent is extended or adjusted under 35 U.S.C. 154(b) by 1272 days.

(21) Appl. No.: 11/156,630

(22) Filed: Jun. 21, 2005

(65) Prior Publication Data

US 2006/0004246 A1    Jan. 5, 2006

Related U.S. Application Data

(60) Provisional application No. 60/580,727, filed on Jun. 21, 2004, provisional application No. 60/602,647, filed on Aug. 19, 2004.

(51) Int. Cl.
*A61F 2/48* (2006.01)
*A61F 2/00* (2006.01)
*A61F 2/02* (2006.01)

(52) U.S. Cl. ........................................... 600/29; 600/30

(58) Field of Classification Search ............. 600/29–31, 600/38–41; 604/327, 328, 329; 128/885, 128/DIG. 25; 606/151–158, 191–193, 197, 606/198, 300; *A61F 2/00, 2/02*
See application file for complete search history.

(56) References Cited

U.S. PATENT DOCUMENTS

| | | | | |
|---|---|---|---|---|
| 3,768,102 A | | 10/1973 | Kwan-Gett et al. ................. 3/1 |
| 3,903,894 A | * | 9/1975 | Rosen et al. ................... 600/31 |
| 4,968,294 A | | 11/1990 | Salama ......................... 600/30 |
| 4,994,019 A | * | 2/1991 | Fernandez et al. ............. 600/30 |
| 5,518,504 A | * | 5/1996 | Polyak ...................... 623/14.13 |
| 5,888,188 A | | 3/1999 | Srougi et al. ................... 600/30 |
| 6,349,727 B1 | | 2/2002 | Stewart, Jr. ................. 128/885 |
| 6,464,628 B1 | | 10/2002 | Forsell ......................... 600/30 |
| 6,502,578 B2 | * | 1/2003 | Raz et al. ..................... 128/898 |
| 6,527,701 B1 | | 3/2003 | Sayet et al. .................... 600/30 |
| 6,609,522 B2 | | 8/2003 | Cheng et al. ................ 128/885 |
| 6,635,058 B2 | * | 10/2003 | Beyar et al. ................. 606/232 |
| 6,691,711 B2 | | 2/2004 | Raz et al. ..................... 128/898 |
| 6,702,827 B1 | * | 3/2004 | Lund et al. ................... 606/151 |
| 2006/0252980 A1 | * | 11/2006 | Arnal et al. ................... 600/29 |

* cited by examiner

*Primary Examiner*—Charles A Marmor, II
*Assistant Examiner*—Catherine E Burk
(74) *Attorney, Agent, or Firm*—Dykema Gossett PLLC

(57) ABSTRACT

An incontinence device for attachment to the inferior ischio-pubic rami in the anterior perineal triangle of a user. The device may include a generally semi-flexible bi-parabolic membrane configured to deflect from an engaged position in which the device exerts pressure upon the user's urethra, or a similar anatomical part. The membrane may deflect to a disengaged position with a first force applied by the user, and be configured to deflect back to the engaged position from the disengaged position upon a further second force applied by the user. Additionally, the device may include bolster connected to the membrane. The bolster may exert pressure upon the user's urethra, or similar anatomical part, when the membrane is in the engaged position and relieve pressure when the membrane is in the disengaged position.

15 Claims, 16 Drawing Sheets

SURGICALLY IMPLANTABLE PERINEAL URINARY INCONTINENCE DEVICE

RELATED APPLICATIONS

The present application claims the benefit of priority to Provisional Application Ser. Nos. 60/580,727, filed Jun. 21, 2004, and 60/602,647, filed Aug. 19, 2004.

BACKGROUND OF INVENTION a. Field of Invention

The invention relates generally to the treatment of involuntary urinary incontinence, and, more particularly to a surgically implantable device operable by a user to prevent or allow bladder emptying by the application of predetermined forces on the device.

b. Description of Related Art

In the art, there presently exist a variety of known surgical treatments for incontinence. Typical surgical treatments include the removal of prostatic obstruction, periurethral injections of obstructive collagen, nerve de-enervation, insertion of artificial urinary sphincters, supporting the urethral-vesical angle with pubovaginal slings and various other methods of surgical urethral bladder neck suspension. In males, while external condom catheters, penile/urethral clamps or indwelling bladder catheters have been used as the simplest therapeutic solutions, these solutions have been both psychologically and operationally deficient for a patient.

Of the aforementioned surgical incontinence treatments, pelvic sling procedures generally use a mesh material for compressing the urethra. Artificial urinary sphincters typically surround the urethra completely, and include an attached separate fluid reservoir implanted in the pelvis. The surgical procedure of urethral bladder neck suspension corrects the position of the bladder and urethra by sewing the bladder neck and urethra directly to the surrounding pelvic bone or nearby structures. These procedures are problematic due to the requirement of extensive surgical dissection for insertion, the propensity for mechanical failure and leaks, and difficulty in the operation of the devices associated with the procedures. Further, these procedures often require post-operative surgical intervention and/or repair in nearly one-half of the patients.

Known prior incontinence treatments are disclosed for example in U.S. Pat. No. 5,888,188 to Srougi et al., U.S. Pat. No. 6,691,711 to Raz et al., and U.S. Pat. No. 6,609,522 to Cheng et al., the respective disclosures of which are incorporated herein by reference.

U.S. Pat. No. 5,888,188 to Srougi et al., as shown in FIG. 1 thereof, discloses a mechanical sphincter device 1 including a semi-annular piece 2. Attached to the semi-annular piece 2 are two strips 3 configured to surround a urethra when sphincter 1 is surgically implanted in a user's urethra. In use, sphincter 1 prohibits passage of urine through the urethra unless the user compresses the sphincter. More specifically, as shown in FIG. 4, a user applies pressure upon the free ends of semi-annular piece 2, causing loosening of the two strips 3 to release the flow of urine through the urethra.

An exemplary drawback of the mechanical sphincter of Srougi et al. is that the urethra is completely surrounded when the sphincter is in the resting position. More importantly, any device that completely surrounds the urethra poses a threat of ischemic injury and is prone to mechanical failure and leaks. Additionally, use of mechanical sphincter 1 requires consistent opposing forces by at least two digits of the user during the release of urine. The present invention thus purports to overcome at least the aforementioned exemplary drawbacks of the treatment disclosed by Srougi et al.

Another type of surgical treatment is disclosed by U.S. Pat. No. 6,691,711 to Raz et al. As shown in FIG. 12 of Raz et al., the surgical treatment includes the insertion and anchoring of a "hammock-like" sling material to bone anchors. The sling material is configured to compress against the bulbar urethra.

While the surgical treatment of Raz et al. overcomes some of the noted drawbacks of the surgical treatment disclosed by Srougi et al., there is no user control. Thus, the surgical treatment of Raz et al. causes permanent compression of the urethra without user control.

Lastly, in U.S. Pat. No. 6,609,522 to Cheng et al, as illustrated in FIG. 1, the incontinence treatment disclosed is an external urethral compression device 10. The device includes an arced structure 12 which acts to compress a urethra when worn by a user as shown in FIG. 3. While the user may have one handed control of the incontinence treatment, external urethral compression devices are prone to urine leakage and may prevent blood circulation to the penis, and most importantly, can be painful when used for extended periods of time.

It would therefore be of benefit to provide a treatment for incontinence including urethral compression and having user controls designed for a first user touch to disengage urethral compression and a second user touch to re-engage urethral compression. It would also be of benefit to provide a surgical treatment that refrains from completely surrounding the urethra. There also remains a need for a surgical treatment which is less prone to mechanical failure, simpler and more economical to manufacture, less invasive to insert, and has superior comfort than the prior art treatment techniques.

SUMMARY OF INVENTION

The invention solves the aforementioned problems and overcomes the drawbacks and deficiencies of prior art surgical treatments for incontinence by providing a device which does not completely surround the urethra or similar anatomical part, while providing for efficient user control.

Thus an exemplary object of the present invention is to provide a device which refrains from completely surrounding the urethra, which may result in the loss of blood flow and risk ischemic injury.

Another exemplary object of the present invention is to provide a user control of the device that is simpler, requires fewer applications of force, and functions superior to those of the prior art.

The present invention achieves the aforementioned exemplary objects by providing a urinary incontinence device for surgical attachment to a user's inferior ischio-pubic rami in the anterior perineal triangle. The device may include a generally semi-flexible bi-parabolic membrane configured to deflect from an engaged position in which the device exerts pressure upon the user's urethra to a disengaged position in which the device permits urinary flow through the user's urethra upon the application of a first force by the user. The membrane may be further configured to deflect back to the engaged position from the disengaged position upon the application of a second force by the user. The membrane may include first and second surfaces, first and second ends, and a fulcrum intermediate the first and second ends. The device may further include a bolster operatively connected to the first surface for exerting pressure upon the user's urethra when the membrane is in the engaged position and relieving pressure from upon the urethra when the membrane is in the disengaged position.

For the device described above, the first and second ends may each be operatively connected to rigid rods which are attached to the user's inferior ischio-pubic rami. The bolster may be inflatable and/or movably connected for facilitating adjustability of the device for different users, and/or include radio-opaque fluid for permitting postoperative observation. The membrane may be substantially free from encircling the user's urethra. The device may be adjustable to the size of a user's anterior perineal triangle with the assistance of reconstructed CATSCANs. The first and second ends may each be operatively connected to rigid rods, and at least one further rigid rod may be inserted into the membrane adjacent the fulcrum for facilitating pivotal movement of the first and second surfaces about the further rod. The first force may be applicable adjacent the first surface, and the second force is applicable adjacent the second surface. The device may also include a tab connected to the second surface for facilitating engagement and disengagement of the device by a means of a user grasping the tab.

The invention also provides a device for compression of a user's anatomical part. The device may include a membrane configured to deflect between engaged and disengaged positions upon the application of a predetermined force on the membrane. The device may further include a bolster either operatively connected to the membrane or formed with the membrane, and capable of exerting pressure upon substantially less than 50% of the user's anatomical part to compress the anatomical part in the engaged position and/or prevent passage of fluid through the anatomical part.

For the device described above, the membrane may include first and second ends each operatively connected to rigid rods which are attached to the user's inferior ischio-pubic rami. The device may engage a urethra, an ischio-cavernous muscle, a crura, or a rectal ampulla. The bolster may be inflatable and/or movable for facilitating adjustability of the device for different users, and/or include radio-opaque fluid for permitting postoperative observation. The device may be adjustable to the size of a user's anterior perineal triangle with the assistance of reconstructed CATSCANs. The membrane may include first and second ends each operatively connected to rigid rods, and at least one further rigid rod inserted into the membrane at a fulcrum disposed generally intermediate the first and second ends for facilitating pivotal movement of first and second surfaces of the membrane about the further rod. The device may also include a first force point at which a first force is applicable adjacent the first surface disposed on one side of the fulcrum to deflect the membrane to the engaged position, and a second force point at which a second force is applicable adjacent the second surface disposed on a second opposite side of the fulcrum to deflect the membrane to the disengaged position. A tab may be connected to the second surface for facilitating engagement and disengagement of the device by a means of a user grasping the tab.

The invention yet further provides a method for obstructing the passage of fluid through a user's anatomical part. The method may include implanting a generally semi-flexible bi-parabolic membrane configured to deflect from an engaged position in which the device exerts pressure upon the user's anatomical part to a disengaged position in which the pressure upon the user's anatomical part is removed by a first force applied by the user. The membrane may be configured to deflect back to the engaged position from the disengaged position upon a second force applied by the user. The method may also include fixing the membrane to at least one rigid rod fixed to the user, applying static resistance on the user's anatomical part to prevent passage of fluid when the membrane is in the engaged position, and relieving static resistance from the user's anatomical part to allow passage of fluid when the membrane is in the disengaged position.

For the method described above, the step of applying static resistance may include applying resistance to the user's urethra, ischio-cavernous muscle, a crura, or a rectal ampulla, and using the device for urinary incontinence, sexual dysfunction or anal incontinence. The method may also include determining the user's urethral occlusive pressure point. The step of implanting a generally semi-flexible bi-parabolic membrane may include implanting a bolster either operatively connected to the membrane or formed with the membrane. The method may also include inflating and adjusting the bolster, with the device being adjustable to the size of the user with the assistance of reconstructed CATSCANs. The method may yet further include grasping and moving a tab connected to the device for facilitating engagement and disengagement of the device.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE PREFERRED EMBODIMENT

Figure 1:
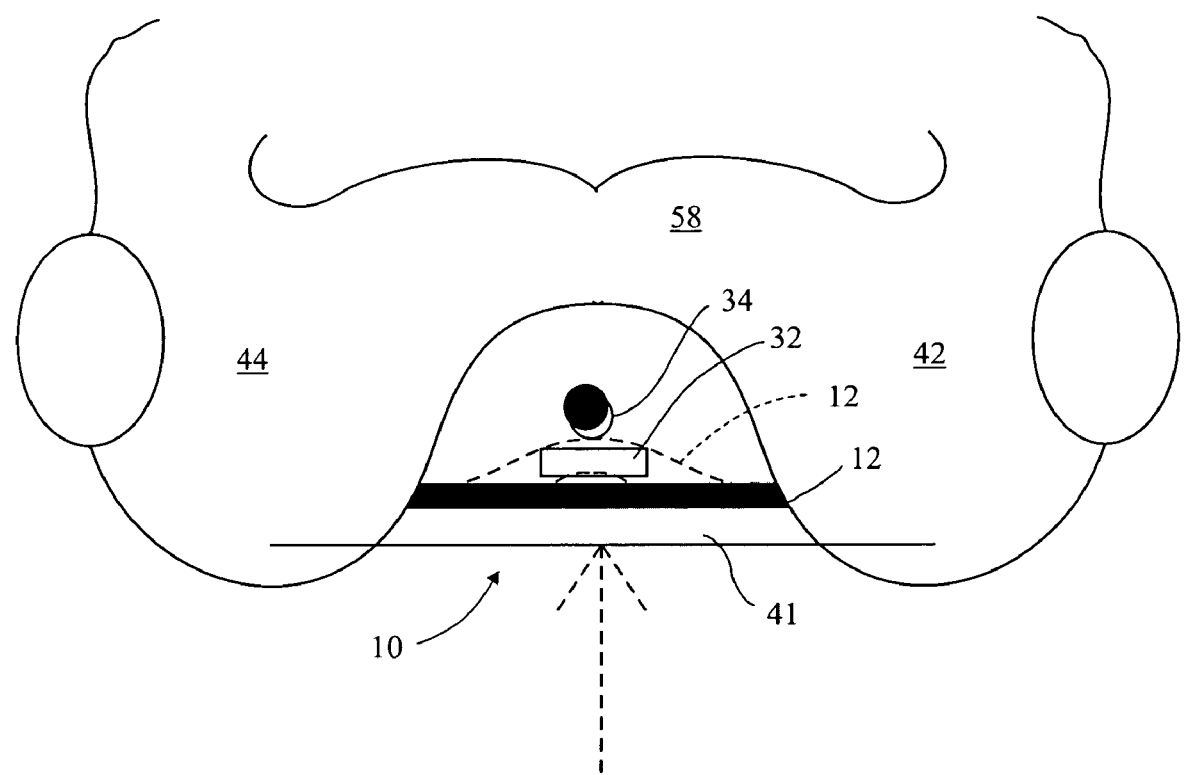
FIG. 1 is an illustrative view of a first embodiment of an incontinence device according to the present invention, as viewed when looking directly at a user.

Referring now to the drawings wherein like reference numerals designate corresponding parts throughout the several views, FIGS. 1-6 illustrate a first embodiment of an incontinence device subject to user control without encircling or completely surrounding an anatomical part, the device being generally designated incontinence device 10, FIGS. 7-11 include illustrations of various CATSCAN reconstructions for facilitating implantation of device 10, and FIGS. 12-15 illustrate a second embodiment of an incontinence device according to the present invention, generally designated incontinence device 100.

Figure 2:
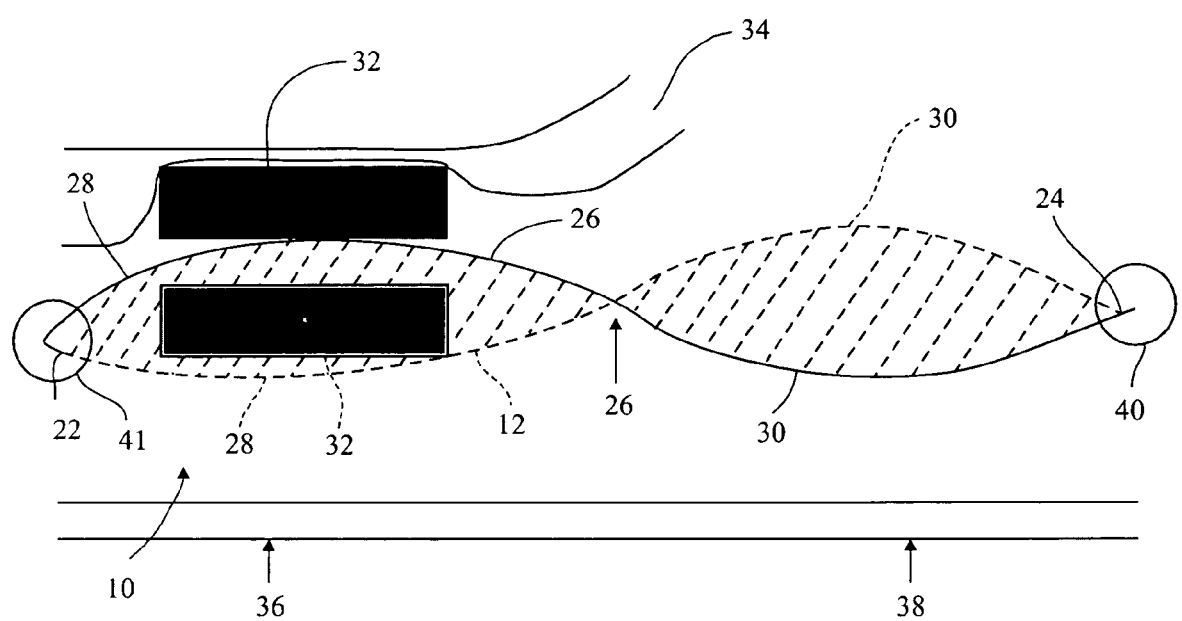
FIG. 2 is an enlarged illustration of the incontinence device of FIG. 1, illustrating the various contours of a generally semi-flexible bi-parabolic membrane and bolster, as viewed when looking from the left or right side of a user.
Figure 3A:
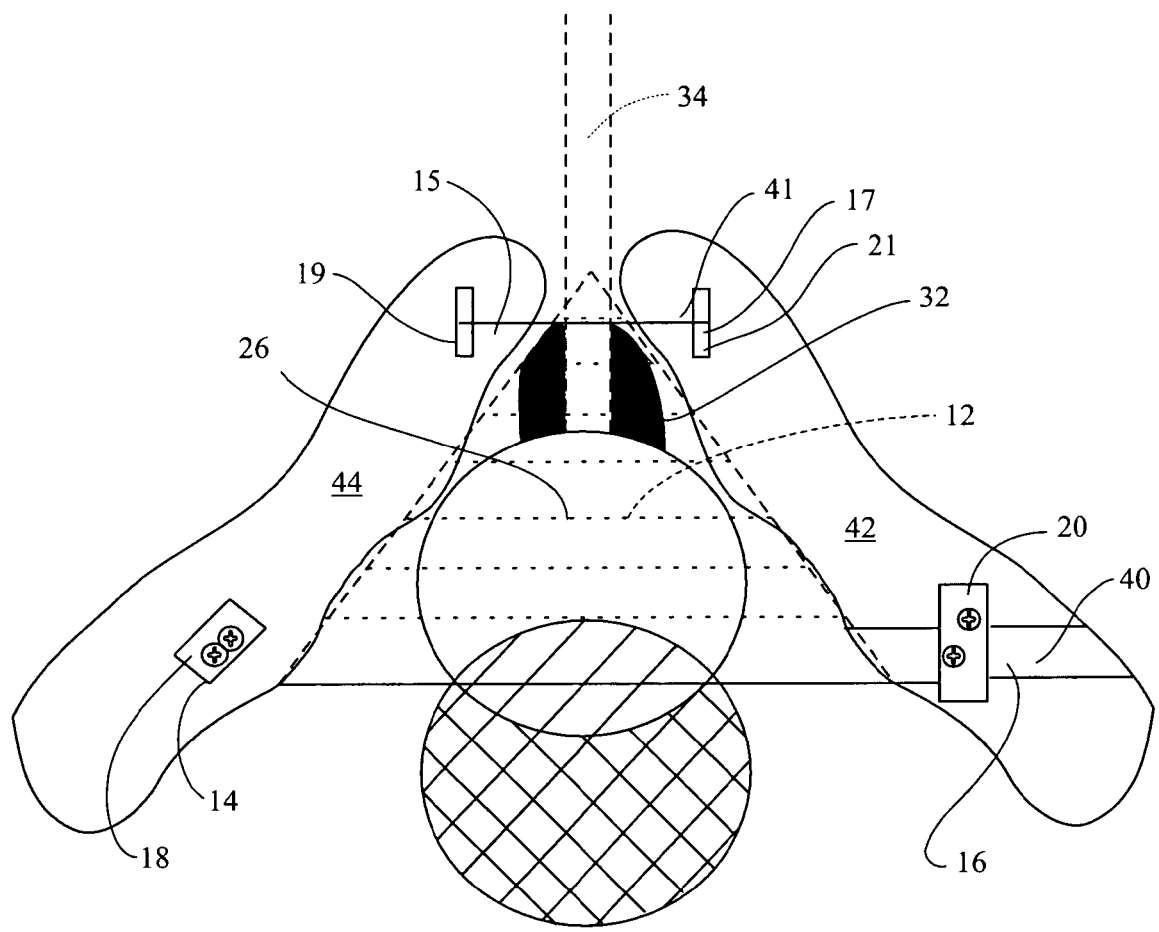
FIGS. 3a and 3b are illustrative views of the incontinence device of FIG. 1, illustrating the various contours of two rigid rods and the generally semi-flexible bi-parabolic membrane, as viewed when looking in an upwards direction at a user.
Figure 3B:
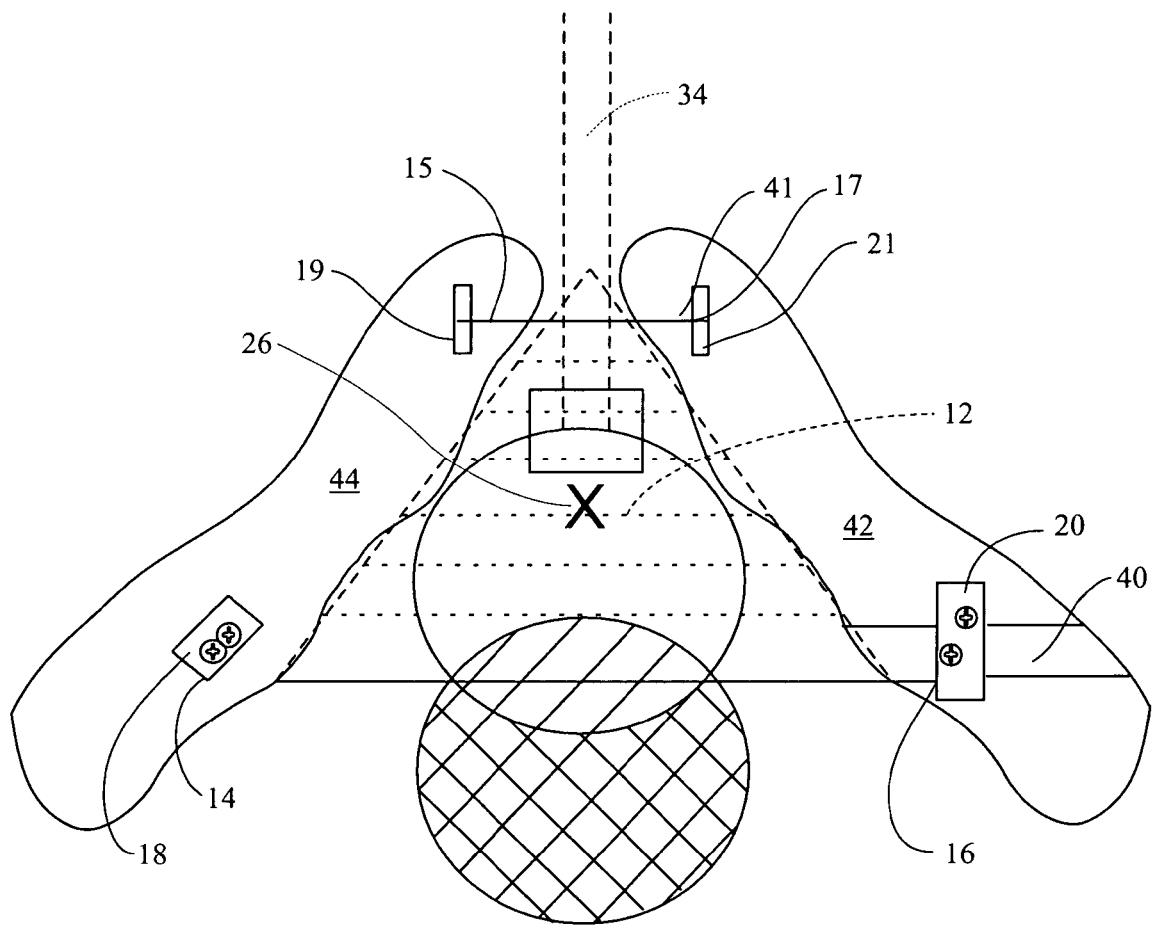

Specifically, as shown in FIGS. 1-3, the first embodiment of incontinence device 10 may include a generally semi-flexible bi-parabolic membrane 12 having opposing ends 24, 22 thereof secured respectively to rods 40, 41 as discussed below. Membrane 12 may be formed of a flexible synthetic material for permitting bending of the membrane about a central fulcrum 26 and include a generally triangular shape (see FIGS. 3a, 3b). Membrane 12 may also be composed of two sections 28, 30, with the sections being disposed on opposite sides of the fulcrum as shown for providing a bi-stable structure on either sides of the fulcrum. Device 10 may include a compressible but substantially firm bolster 32 operatively connected to section 28, or otherwise formed with section 28, for pressing against a user's urethra 34 or other anatomical part. Bolster 32 may be formed of a substantially rigid synthetic material for enabling uniform compression of urethra 34. While bolster 32 is illustrated as being operable by device 10 including fulcrum 26, instead of a fulcrum, the bolster may be attached to section 28 by means of a ratchet (not shown) or a moveable slide (not shown) for permitting movement of the bolster to prevent or allow passage of fluid through urethra 34.

As shown in FIGS. 1 and 2 (especially FIG. 2), membrane 12 may be disposed in an engaged position (shown in solid) in which the membrane exerts pressure on urethra 34 by means of bolster 32, and otherwise be disposable in a disengaged position (shown in dashed) for allowing passage of fluid through the urethra. As described in greater detail below, device 10 may include predetermined force points 36, 38 adjacent sections 28, 30, respectively, for permitting occlusion (shown in solid) or relaxation (shown as dashed) of bolster 32 relative to the urethra.

Referring now to FIGS. 2, 3a and 3b, as briefly discussed above, device 10 may include rigid rods 40, 41 secured to inferior ischio pelvic pubic rami 42, 44, which together form a ladder-type structure as shown. Membrane 12 may be fixed to rods 40, 41, whose respective opposing ends 14, 16 and 15, 17 are secured by respective bone anchors 18, 20 and 19, 21 to inferior ischio pelvic pubic rami 44, 42. Membrane 12 may be fixed to rods 40, 41 by threading and the like to prevent the membrane from moving out of position, yet allowing for sufficient flexibility of the membrane for deflection at force points 36, 38 in the anterior perineal triangle, both in front of the midpoint and behind the midpoint of the membrane. Rods 40, 41 may be formed of a non-corrosive metal (i.e. stainless steel) or synthetic material, and may be screwed or otherwise embedded with bone anchors into the inferior pelvic ischio-pubic rami as shown or held with bone cement (i.e. polymethyl methacrylate glue).

The implantation and operation of incontinence device 10 will now be described in detail with reference to FIGS. 1-11.

Referring to FIGS. 1-4, incontinence device 10 may be implanted above a portion of a user's perineum skin 46, and below a pubis 48. As briefly discussed above, in the position of FIG. 4, device 10 may be implanted by having its opposing ends 24, 22 secured to rods 40, 41, which are further secured by respective bone anchors 18, 20 and 19, 21 to inferior ischio pelvic pubic rami 44, 42. Device 10 may be fixed to a user's pelvis bones by means of rods, screws, bone cement and/or plates utilizing individualized CATSCAN computations of areas and dimensions provided by a 3-D computer program prior to surgery.

Specifically, as shown in FIGS. 7-11, each potential user of device 10 may be individually scanned, and his/her anatomy determined pre-operatively in a computerized dimensional and volumetric plane to enable measurements to be made to virtually fit the individual with device 10 prior to any incision. The bone fixation provides a surface against which resistance to urinary flow is maintained in the triangle between ischio-pubic rami 42, 44 and pubic symphysis when activated by a user.

Figure 7:
FIG. 7 includes an illustration of an anterior oblique CATSCAN reconstruction for facilitating implantation the incontinence device of FIG. 1.
Figure 8:
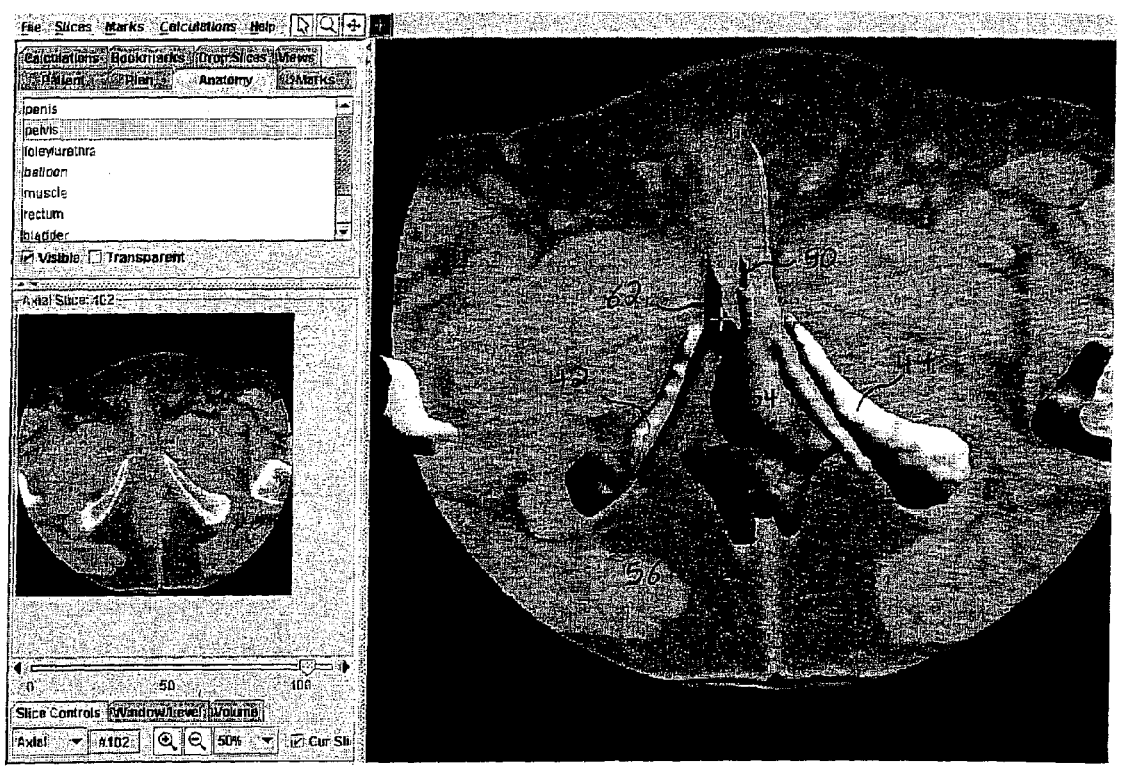
FIG. 8 includes an illustration of a transverse CATSCAN slice for facilitating implantation the incontinence device of FIG. 1.
Figure 9:
FIG. 9 includes an illustration of an inferior posterior oblique pelvic CATSCAN reconstruction for facilitating implantation the incontinence device of FIG. 1.
Figure 10:
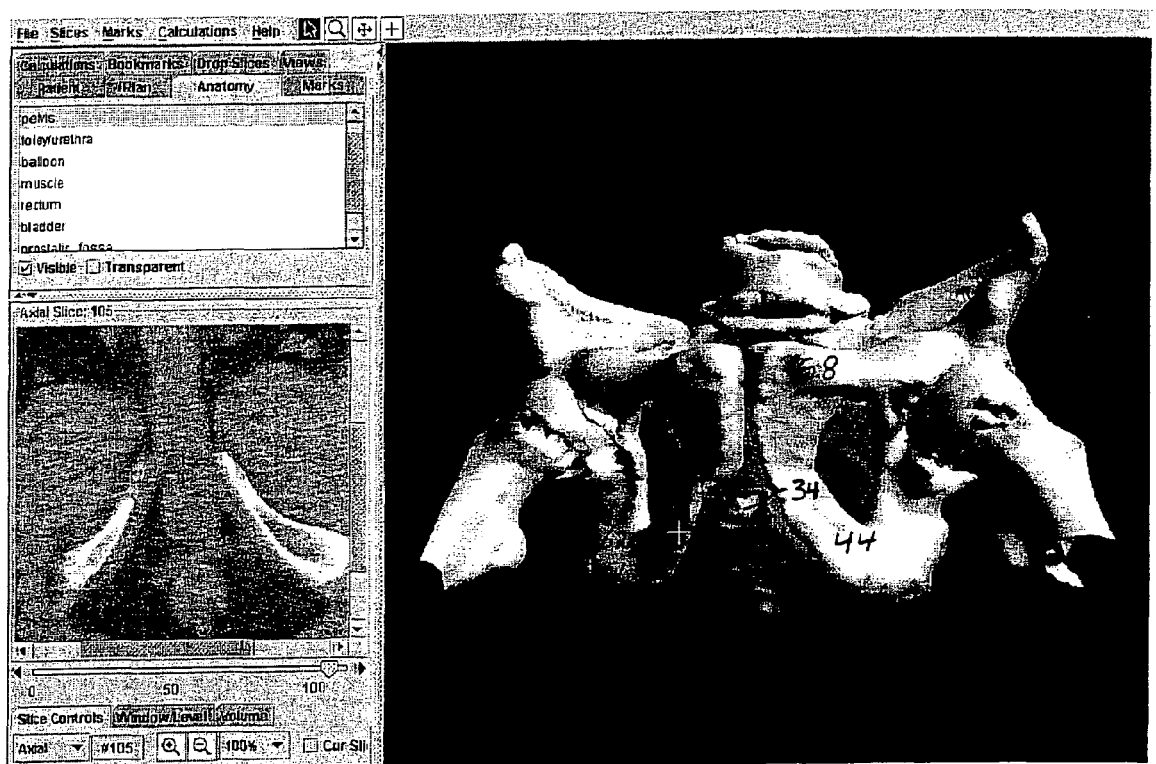
FIG. 10 includes an illustration of an anterior pelvic CATSCAN reconstruction for facilitating implantation the incontinence device of FIG. 1.
Figure 11:
FIG. 11 includes an illustration of a posterior inferior pelvic CATSCAN reconstruction for facilitating implantation the incontinence device of FIG. 1.

Referring to FIGS. 7 and 8 for example, the CATSCAN illustrates urethra 34, catheter 50, inferior pelvic rami 42, 44, superior pubic ramus 52, bladder 54, rectum 56, symphysis pubis 58, sacrum 60 and site of recommended incontinence device insertion at 62. FIGS. 9-11, which have been briefly described above, provide similar notations and location 62 being the site of recommended incontinence device insertion. In an exemplary use of the CATSCANs of FIGS. 7-11, the Pelvic Girdle CATSCANs of FIG. 9 provides a reconstructed view a surgeon may encounter in the perineal triangle with the catheterized urethra, prostatourethral junction and sphincter between the ischio-pubic bones. In FIG. 9, rectum 56 is located between the prostate and sacrum. A similar view of the structures is noted in a CATSCAN slice at the same anatomic level where device 10 would be anchored. A surgeon may make a precise measurement from a bone anchor site to the corresponding site on the opposite bony ramus by imposing an "X" at 62 on the computer scan and producing a calculation (see FIGS. 7-11). By following the CATSCAN reconstructions (see FIGS. 10 and 11), the triangulation of the urethra can be appreciated for bolster pressure application by device 10. As shown in FIGS. 9-11, a review of the CATSCAN reconstruction from an obliquely inferior viewpoint (i.e. with all structures except the bones, urethra catheter and prostate subtracted by the computer) shows that the urethra and prostatourethral junction (sphincteric area) would be juxtapositioned beneath the pubic symphysis in position to be compressed from below by the bolster pushing upwards.

Figure 4:
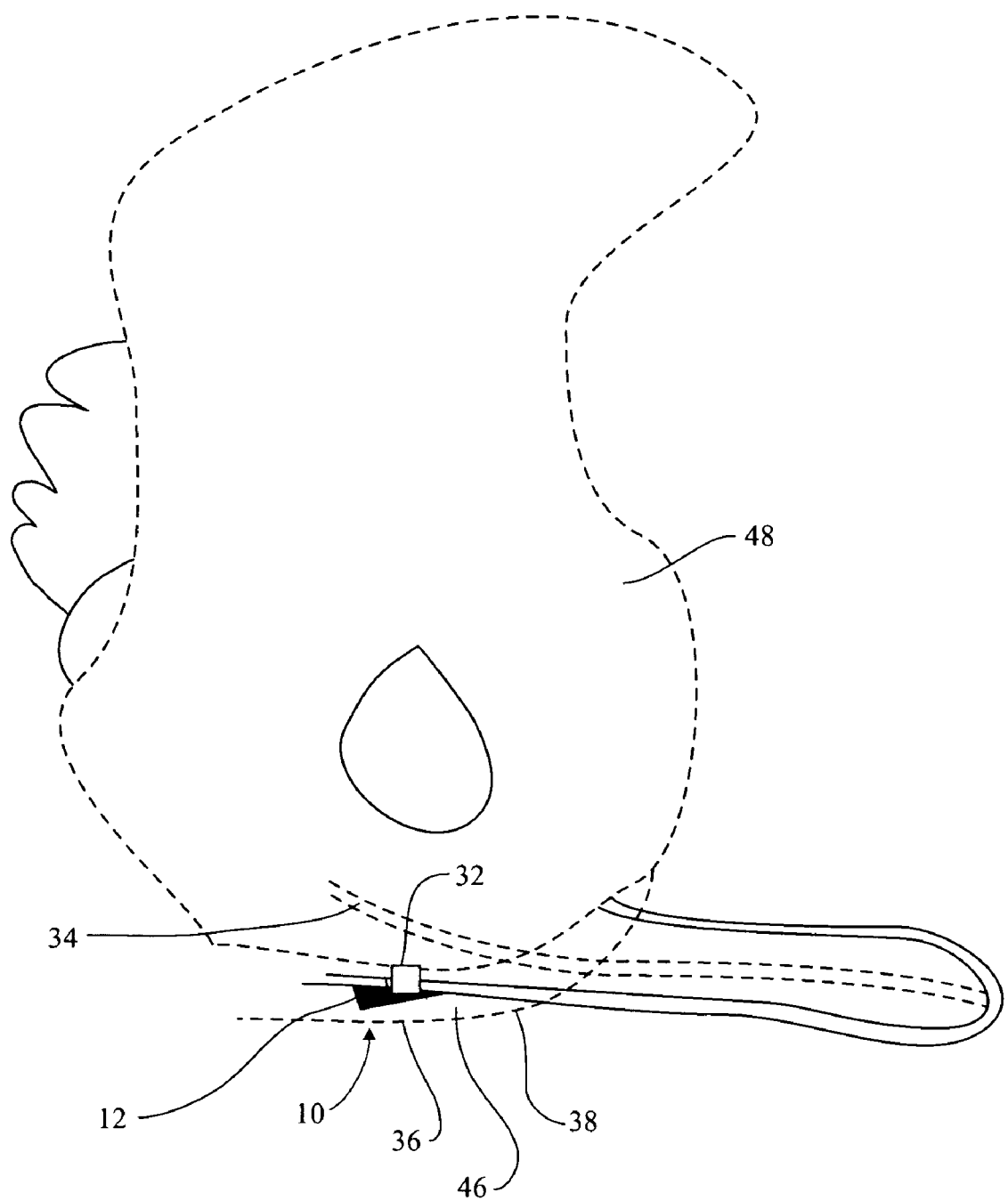
FIG. 4 is a sectional view of a male pelvis, illustrating the general implant location of the incontinence device of FIG. 1.
Figure 5:
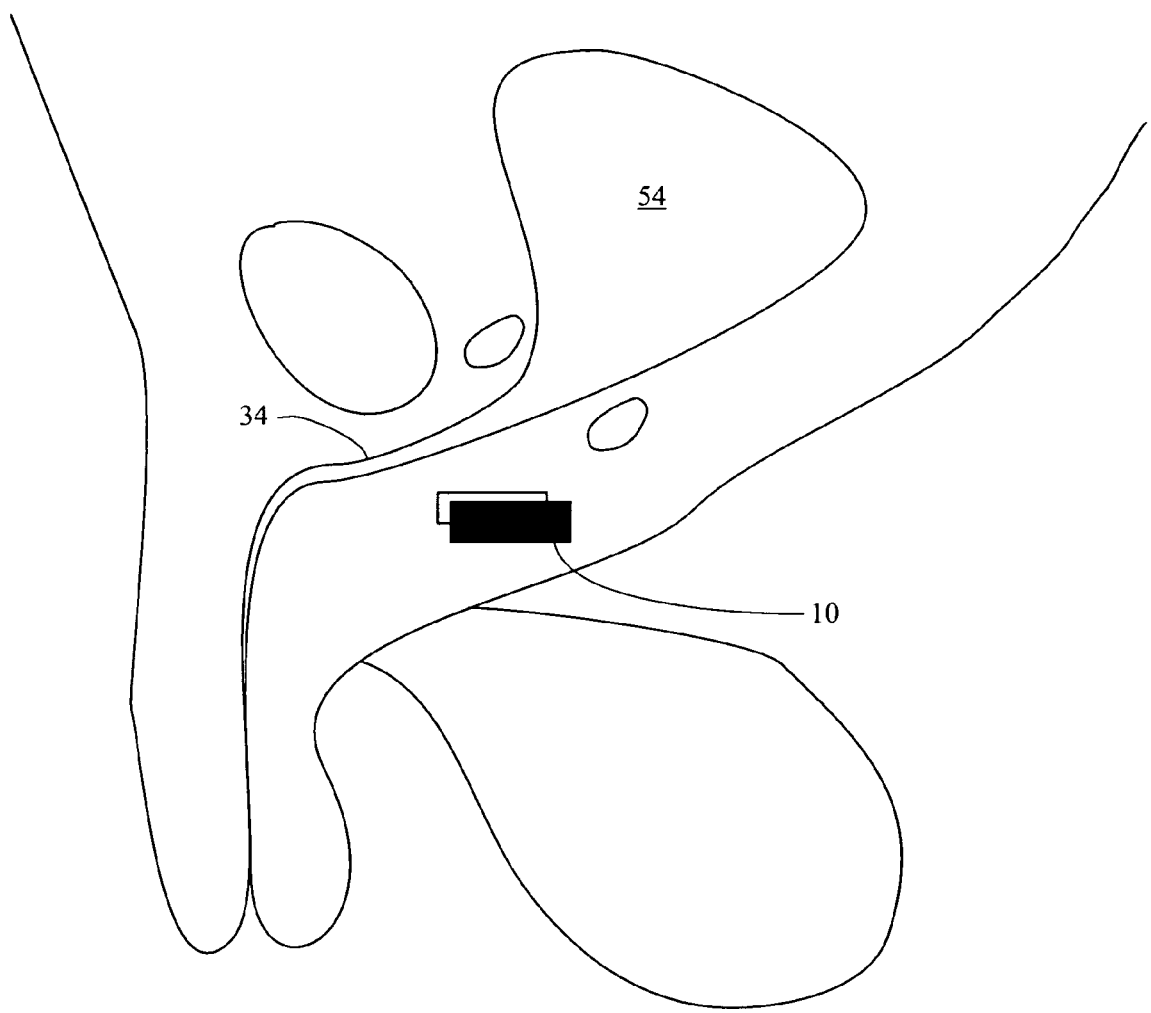
FIG. 5 is another sectional view of a male, illustrating the general implant location of the incontinence device of FIG. 1.
Figure 6:
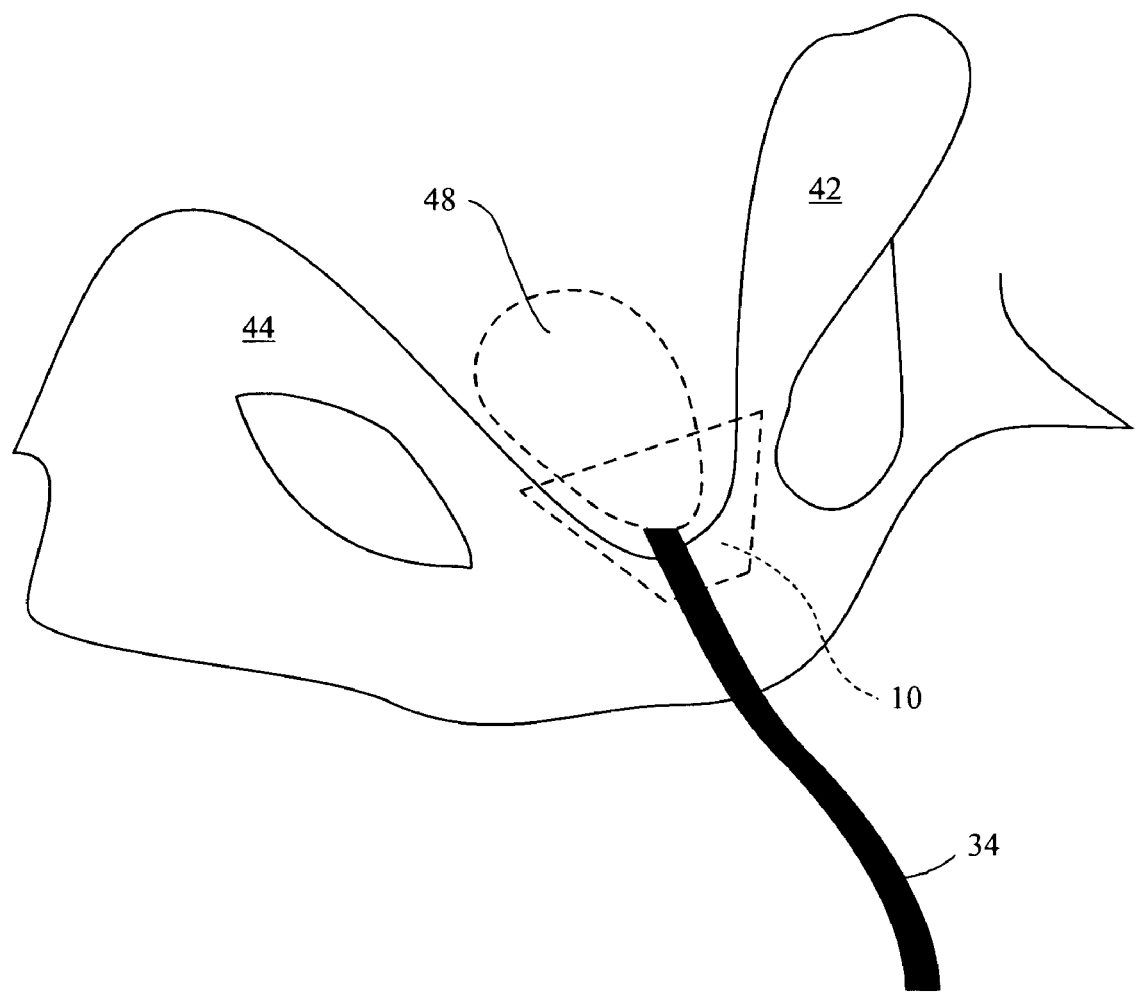
FIG. 6 is an illustrative view of the generally semi-flexible bi-parabolic membrane of the incontinence device in FIG. 1 positioned to apply pressure to a portion of a urethra.

In use, with device 10 disposed in the implanted position of FIG. 4 (see also FIG. 2), a user may simply apply a force through a portion of perineum skin 46 around force point 36 to engage membrane 12 and thus apply pressure onto urethra 34 by means of bolster 32. Further, pressure may be applied by the user through perineum skin 46 around force point 38 to disengage membrane 12 and enable free urinary flow upon demand. As illustrated in FIGS. 4 and 5, incontinence device 10 may be implanted in proximity of urethra 34 for occluding fluid released from bladder 54. As shown in FIG. 6, device 10 may be located between inferior ischio pubic rami 42, 44 so as to triangulate urethra 34. As illustrated in FIG. 2, membrane 12 rotates about fulcrum 26 but remains in its final parabolic position because of internal tension until displaced by the user.

The second embodiment of incontinence device 100 will now be described in detail with reference to FIGS. 12-15.

Figure 12:
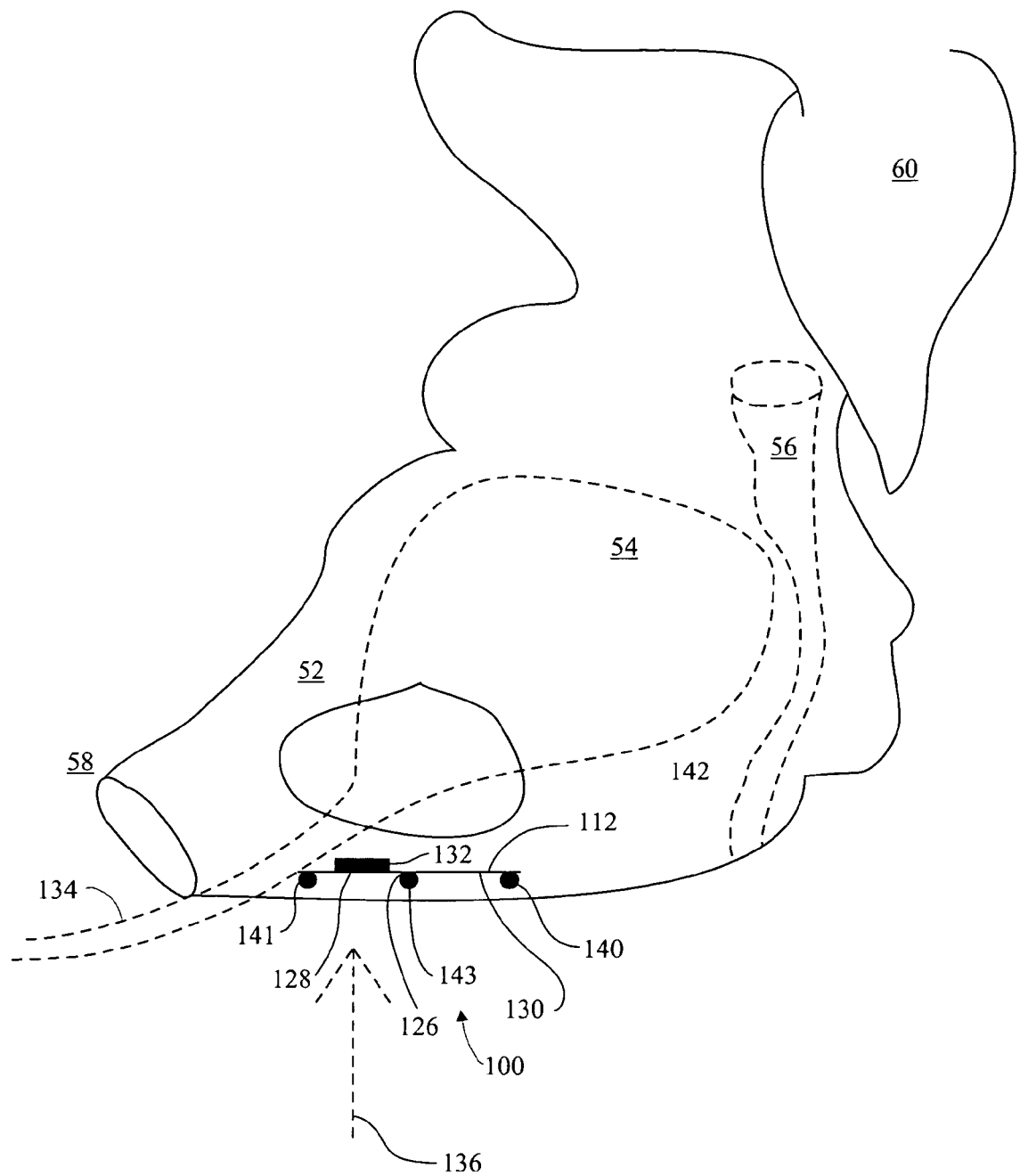
FIG. 12 is an illustrative view of a second embodiment of an incontinence device according to the present invention, as viewed when looking from the left side of a user.
Figure 13:
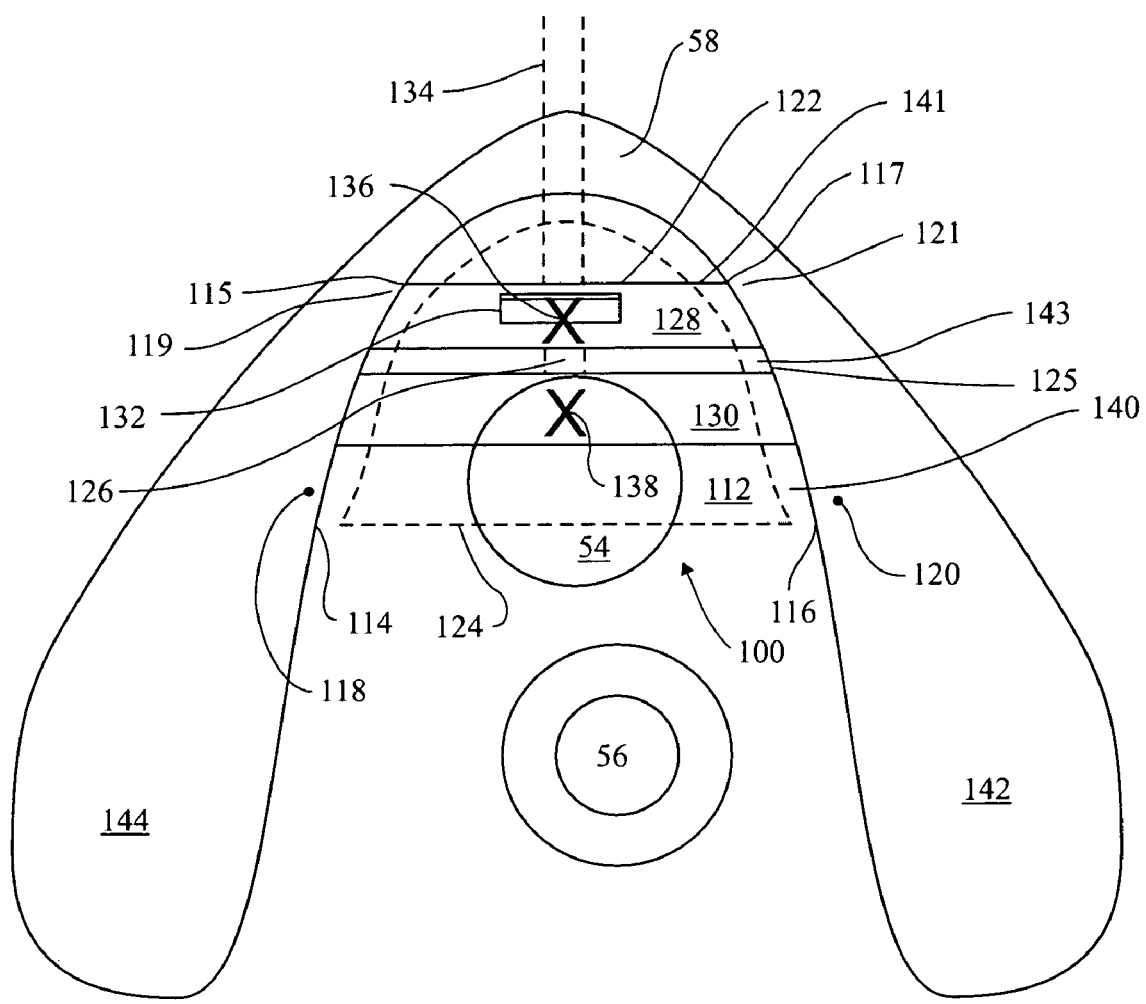
FIG. 13 is an illustrative view of the second embodiment of an incontinence device of FIG. 12, illustrating the various contours of three rigid rods and the generally semi-flexible bi-parabolic membrane, as viewed when looking in an upwards direction at a user.

Referring to FIGS. 12-13, the second embodiment of incontinence device 100 may include a generally semi-flexible bi-parabolic membrane 112 having opposing ends 124, 122 thereof secured respectively to rods 140, 141 as discussed below. Membrane 112 may be formed of a flexible synthetic material for permitting bending of the membrane about a central fulcrum 126 and include a generally triangular shape (see FIG. 13). Fulcrum 126 may include a third rigid rod 143 inserted through a ferrule (not shown) in the membrane. Rod 143 may be inserted as shown in FIGS. 12 and 13, while still allowing the membrane to remain flexible enough to be deflected with perineal pressure by a user at force points 136, 138, as described below. Rod 143 may also provide mid-stability to bi-concave flexible membrane 112 about the pivot of fulcrum 126, thus maintaining device 100 in a desired position about fulcrum 126. Membrane 112 may also be composed of two sections 128, 130, with the sections being disposed on opposite sides of the fulcrum as shown for providing a bi-stable structure on either sides of the fulcrum. Device 100 may include a compressible but substantially firm bolster 132 operatively connected to section 128, or otherwise formed with section 128, for pressing against a user's urethra 134 or other anatomical part. Bolster 132 may be formed of a substantially rigid synthetic material for enabling uniform compression of urethra 134. While bolster 132 is illustrated as being operable by device 100 including fulcrum 126, the bolster may be attached to section 128 by means of a ratchet (not shown) or a moveable slide (not shown) for permitting movement of the bolster to prevent or allow passage of fluid through urethra 134.

As shown in FIGS. 12 and 13, membrane 112 may be disposable in an engaged position (similar to the solid outline for membrane 12 of FIG. 2; see also FIG. 14) in which the membrane exerts pressure on urethra 134 by means of bolster 132, and otherwise be disposable in a disengaged position (similar to the dashed outline for membrane 12 of FIG. 2; see also FIG. 14) for allowing passage of fluid through the urethra. As described in greater detail below, device 100 may include predetermined force points 136, 138 adjacent sections 128, 130, respectively, for permitting occlusion (shown in solid) or relaxation (shown as dashed) of bolster 132 relative to the urethra.

As briefly discussed above, device 100 may include rigid rods 140, 141 secured to inferior ischio pelvic pubic rami 142, 144. Membrane 112 may be fixed to rods 140, 141, whose respective opposing ends 114, 116 and 115, 117 are secured by respective bone anchors 118, 120 and 119, 121 to inferior ischio pelvic pubic rami 144, 142. Rod 143 may be secured at ends 123, 125 thereof to inferior ischio pelvic pubic rami 142, 144 in a like manner as rods 140, 141. Membrane 112 may be fixed to rods 140, 141 by threading and the like to prevent the membrane from moving out of position, yet allowing for sufficient flexibility of the membrane for deflection at force points 136, 138 in the anterior perineal triangle, both in front of the midpoint and behind the midpoint of the membrane. Rods 140, 141 and rod 143 may be formed as circular rods made of a non-corrosive metal (i.e. stainless steel) or synthetic material, and may be screwed or otherwise embedded with bone anchors into the inferior pelvic ischio-pubic rami as shown or held with bone cement (i.e. polymethyl methacrylate glue).

Figure 14:
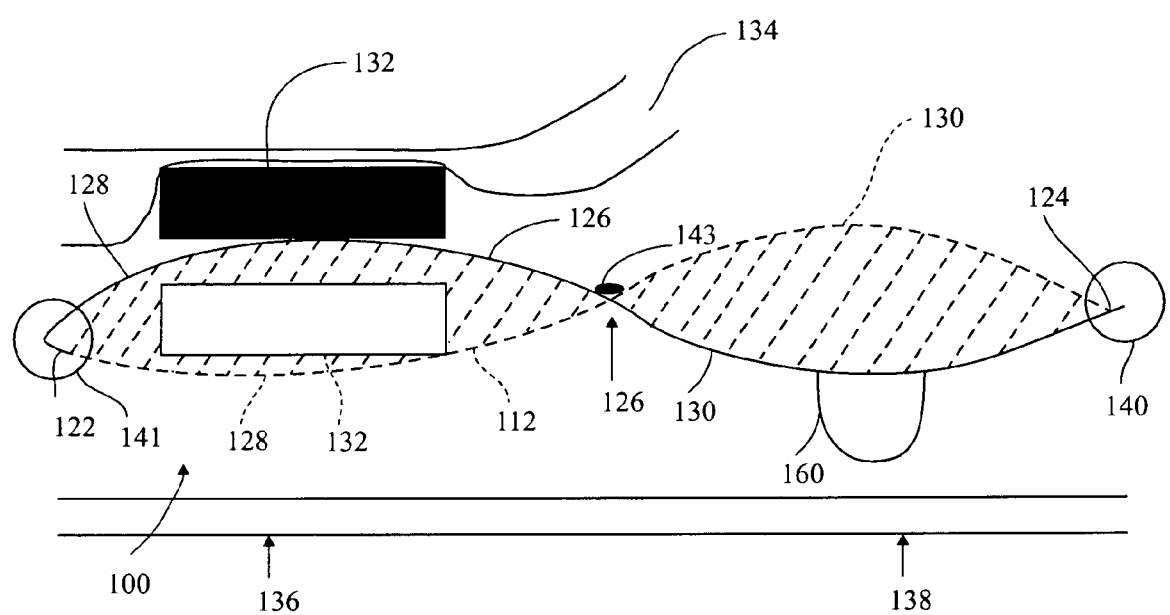
FIG. 14 is an enlarged illustration of the incontinence device of FIG. 12, illustrating the various contours of a generally semi-flexible bi-parabolic membrane and bolster, and a tab for facilitating operation of the device, as viewed when looking from the left or right side of a user.
Figure 15:
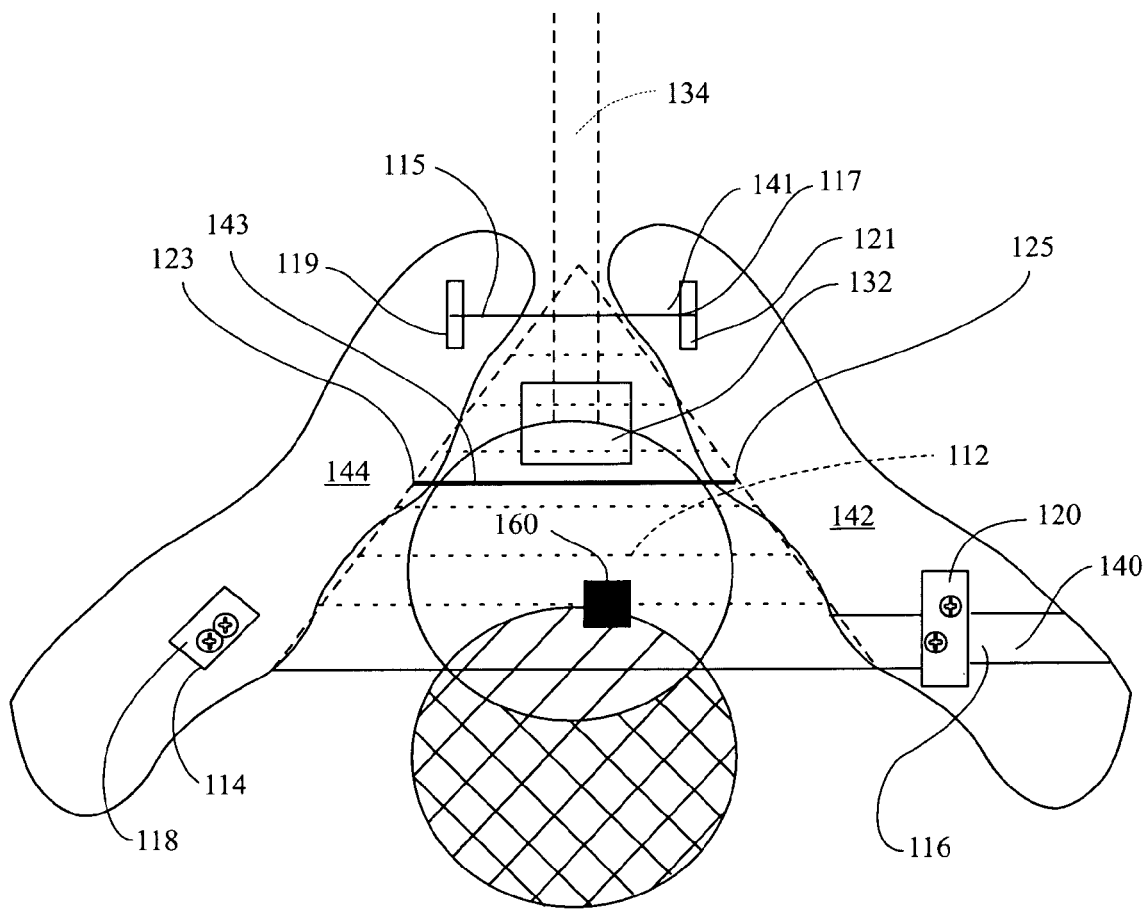
FIG. 15 is an illustrative view of the second embodiment of the incontinence device of FIG. 12, illustrating the various contours of three rigid rods and the generally semi-flexible bi-parabolic membrane, and the tab for facilitating operation of the device, as viewed when looking in an upwards direction at a user.

Referring to FIGS. 14 and 15, device 100 may optionally include a tab 160 on section 130 for facilitating device operation by allowing a user to grasp the tab for downward deflection into the engaged configuration shown in solid in FIG. 14. Tab 160 may be felt through the perineal skin and may also be utilized as a pressure point for upward deflection of the device to the disengaged configuration shown in dashed in FIG. 14. Tab 160 may be made of a soft material to prevent erosion of the underlying skin.

Those skilled in the art would readily appreciate in view of this disclosure that the implantation and operation of incontinence device 100 would be similar to that for device 10, as discussed above with reference to FIGS. 1-11.

Based upon the discussion above, the first and second embodiments of the incontinence devices of the present invention thus solve the problems and overcomes the drawbacks and deficiencies of prior art incontinence devices by providing devices capable of occlusion and relaxation of the urethra based upon user control, without completely surrounding the urethra. Since compression of the urethra is not concentric, devices 10 and 100 are much less likely to cause urethral ischemia.

As discussed above, various modifications may be made to devices 10, 100 without departing from the scope of the present invention.

For example, although devices 10, 100 have been illustrated as being provided on a male in FIGS. 1-15, those skilled in the art would appreciate in view of this disclosure that devices 10, 100 may be likewise fitted to males (as shown in FIG. 4) and females (i.e. by means of a trans-vaginal incision due to the relatively short length of the female urethra) of various ischio pubic size, and may further be used for various other anatomical parts requiring user controlled occlusion and relaxation. For example, although devices 10, 100 have been described for compression of a user's urethra, devices 10, 100 may alternatively be used for compression of an ischio-cavernous muscle, a crura, and/or a rectal ampulla, for treatment of erectile dysfunction or anal incontinence. For anal incontinence, devices 10, 100 may be used by switching positions of bolster 32 (or 132) and posteriorally displacing the device membrane over the ischirectal fossa. Further, whereas devices 10, 100 have been described as being engageable and disengageable by means of a force applied by the user, devices 10, 100 may be readily modified for automatic operation by means of an actuator, such as a magnetic inducer or another electronic actuator, for applying the noted forces for engaging and disengaging the device.

For females, the incontinence devices of the present invention may be used for female urethral hypermobility when the present invention devices are combined with surgical procedures for cystocoele or urethrocoele repair. The use of a static synthetic sling in vaginal retropubic urethropexy further facilitates use of devices 10, 100 in females.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A urinary incontinence device for attachment to a user's inferior ischio-pubic rami in the anterior perineal triangle, the device comprising:
   a generally semi-flexible bi-parabolic membrane configured to deflect from an engaged position in which the device exerts pressure upon the user's urethra to a disengaged position in which the device permits urinary flow through the user's urethra upon the application of a first force by the user, the membrane being further configured to deflect back to the engaged position from the disengaged position upon the application of a second force by the user, the membrane including:
      first and second surfaces,
      first and second ends, and
      a fulcrum intermediate the first and second ends; and
   a bolster operatively connected to the first surface for exerting pressure upon the user's urethra when the membrane is in the engaged position and relieving pressure from upon the urethra when the membrane is in the disengaged position.

2. A device according to claim 1, wherein the first and second ends are each operatively connected to rigid rods which are attached to the user's inferior ischio-pubic rami.

3. A device according to claim 1, wherein the bolster is at least one of inflatable and movably connected for facilitating adjustability of the device for different users.

4. A device according to claim 1, wherein the bolster includes radio-opaque fluid for permitting postoperative observation.

5. A device according to claim 1, wherein the membrane is substantially free from encircling the user's urethra.

6. A device according to claim 1, wherein the device is adjustable to the size of a user's anterior perineal triangle with the assistance of reconstructed CATSCANs.

7. A device according to claim 1, wherein the first and second ends are each operatively connected to rigid rods, and at least one further rigid rod is inserted into the membrane adjacent the fulcrum for facilitating pivotal movement of the first and second surfaces about the further rod.

8. A device according to claim 1, wherein the first force is applicable adjacent the first surface, and the second force is applicable adjacent the second surface.

9. A device according to claim 1, further comprising a tab connected to the second surface for facilitating engagement and disengagement of the device by a means of a user grasping the tab.

10. A method for obstructing the passage of fluid through a user's anatomical part, the method comprising:
    implanting a generally semi-flexible bi-parabolic membrane configured to deflect from an engaged position in which the device exerts pressure upon the user's anatomical part to a disengaged position in which the pressure upon the user's anatomical part is removed by a first force applied by the user, the membrane being further configured to deflect back to the engaged position from the disengaged position upon a second force applied by the user;
    fixing the membrane to at least one rigid rod fixed to the user;
    applying static resistance on the user's anatomical part to prevent passage of fluid when the membrane is in the engaged position; and
    relieving static resistance from the user's anatomical part to allow passage of fluid when the membrane is in the disengaged position.

11. A method according to claim 10, wherein applying static resistance includes applying resistance to one of the user's urethra, ischio cavernous muscle, a crura, and a rectal ampulla, and using the device for one of urinary incontinence, sexual dysfunction and anal incontinence.

12. A method according to claim 10, further including determining the user's urethral occlusive pressure point.

13. A method according to claim 10, wherein implanting a generally semi-flexible bi-parabolic membrane includes implanting a bolster one of operatively connected to the membrane and formed with the membrane.

14. A method according to claim 13, further including inflating and adjusting the bolster, the device being adjustable to the size of the user with the assistance of reconstructed CATSCANs.

15. A method according to claim 10, further comprising grasping and moving a tab connected to the device for facilitating engagement and disengagement of the device.

* * * * *